United States Patent
Lenges et al.

(10) Patent No.: US 6,846,945 B2
(45) Date of Patent: Jan. 25, 2005

(54) PHOSPHONITE LIGANDS AND THEIR USE IN HYDROCYANATION

(75) Inventors: Christian P. Lenges, Wilmington, DE (US); Helen S. M. Lu, Wallingford, PA (US); Joachim C. Ritter, Wilmington, DE (US)

(73) Assignee: Invista North America S.a.r.l., Wilmington, DE (US)

(*) Notice: Subject to any disclaimer, the term of this patent is extended or adjusted under 35 U.S.C. 154(b) by 0 days.

(21) Appl. No.: 10/454,024

(22) Filed: Jun. 4, 2003

(65) Prior Publication Data

US 2003/0212288 A1 Nov. 13, 2003

Related U.S. Application Data

(62) Division of application No. 10/093,655, filed on Mar. 7, 2002, now Pat. No. 6,660,877.

(51) Int. Cl.[7] .............................................. C07C 253/00
(52) U.S. Cl. ....................................... 558/335; 558/332
(58) Field of Search ................................. 558/332, 335; 556/14; 502/162

(56) References Cited

U.S. PATENT DOCUMENTS

| | | | |
|---|---|---|---|
| 3,655,723 | A | 4/1972 | Drinkard, Jr. |
| 5,817,850 | A | 10/1998 | Pastor et al. |
| 6,242,633 | B1 | 6/2001 | Fischer et al. |
| 6,362,354 | B1 | 3/2002 | Bunel et al. |
| 6,437,192 | B1 | 8/2002 | Bunel |

FOREIGN PATENT DOCUMENTS

| | | |
|---|---|---|
| DE | 100 46 025 | 9/2000 |
| DE | 100 46 025 A1 | 9/2000 |
| WO | WO 9843935 | 10/1998 |
| WO | WO 9946044 | 9/1999 |
| WO | WO 9964155 | 12/1999 |

Primary Examiner—Rita Desai
Assistant Examiner—Robert Shiao

(57) ABSTRACT

Disclosed herein are processes for hydrocyanation and isomerization of olefins by using at least one multidentate phosphonite ligands, including organometallic phosphonite ligands with a Group VIII metal or Group VIII metal compound, and optionally, a Lewis acid promoter.

9 Claims, No Drawings

PHOSPHONITE LIGANDS AND THEIR USE IN HYDROCYANATION

CROSS-REFERENCE TO RELATED APPLICATIONS

This application is a divisional of application Ser. No. 10/093,655, originally filed on Mar. 7, 2002 now U.S. Pat. No. 6,660,877, in the names of Christian P. Lenges, Helen S. M. Lu and Joachim C. Ritter.

FIELD OF THE INVENTION

The present invention concerns the use of catalyst compositions comprising a Group VIII metal and a multidentate phosphonite ligand for olefinic hydrocyanation and isomerization processes.

BACKGROUND OF THE INVENTION

Certain phosphonites have been used as a part of hydrocyanation catalyst systems. U.S. Pat. No. 5,817,850 discloses the use of a catalyst composition in hydroformylation and hydrocyanation reactions. WO9843935 discloses the use of certain phosphonite ligands as part of a catalyst system in a process for producing an aldehyde. WO9946044 relates to a hydroformylation process using phosphonite ligands as part of the catalyst system for hydroformylation reactions. U.S. Pat. No. 6,242,633 discloses a process for the production of nitriles using catalysts containing phosphonite ligands. Further, WO9964155 discloses use of catalysts containing phosphorous ligands in hydrocyanation reactions.

Despite the disclosure of various ligands in hydrocyanation and hydroformylation processes. Catalyst compositions comprising certain multidentate phosphonite ligands show effectiveness and/or higher performance and achieve improvements in rapidity, selectivity, efficiency or stability.

SUMMARY OF THE INVENTION

A hydrocyanation process, said process comprising: contacting an ethylenically unsaturated olefin compound with HCN in the presence of a catalyst composition, wherein said catalyst composition comprises a Group VIII metal and a phosphonite ligand wherein the ligand has a structure:

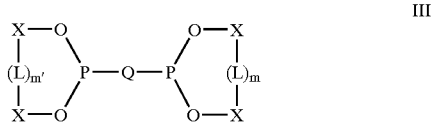
III wherein the X groups are either the same or different unbridged substituted or unsubstituted organic aromatic groups and the substituent on the X groups is independently selected from the group consisting of C1 to C12 alkyl, perflouroalkyl, cycloalkyl, alkoxy, acetal, ketal, alkylaryl, aryl, hetero aryl, cyano, and hydrogen and wherein the Q groups are either a substituted or unsubstituted divalent aromatic or non aromatic hydrocarbon radical and the substituent on the Q groups is independently selected from the group consisting of C1 to C12 alkyl, cycloalkyl, alkoxy, alkylaryl, aryl, hetero aryl, and cyano, and L is a linking group selected from the group consisting of —CR1R2-, —O—, —S—, —CO— (wherein each of R1–R2 are independent of one another, are a hydrogen atom, a C1–12 alkyl group, or an aryl group), and each of m and m' which are independent of each other, are 0 or 1.

The use of a catalyst based on a ligand of structure III for the hydrocyanation and/or the positional isomerization or double bond isomerization of olefins.

DETAILED DESCRIPTION

The present invention describes a hydrocyanation process comprising: contacting an ethylenically unsaturated olefin compound with HCN in the presence of a catalyst composition, wherein the catalyst composition comprises a group VIII metal and a phosphonite ligand having a structure:

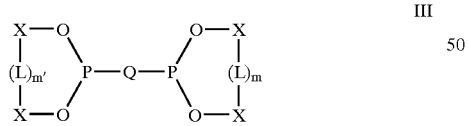
III wherein the X groups are either the same or different unbridged substituted or unsubstituted organic aromatic groups and the substituent on the X groups is independently selected from the group consisting of C1 to C12 alkyl, perfluoroalkyl, cycloalkyl, alkoxy, acetal, ketal, alkylaryl, aryl, hetero aryl, cyano, and hydrogen and wherein the Q groups are either a substituted or unsubstituted divalent aromatic or non aromatic hydrocarbon radical and the substituent on the Q groups is independently selected from the group consisting of C1 to C12 alkyl, cycloalkyl, alkoxy, alkylaryl, aryl, hetero aryl, and cyano, and L is a linking group selected from the group consisting of —CR1R2-, —O—, —S—, —CO—; wherein each of R1–R2 are independent of one another, are a hydrogen atom, a C1–12 alkyl group, or a substituted or unsubstituted aryl group; and each of m and m' independently are 0 or 1.

Typical X for structure III include but are not limited to:

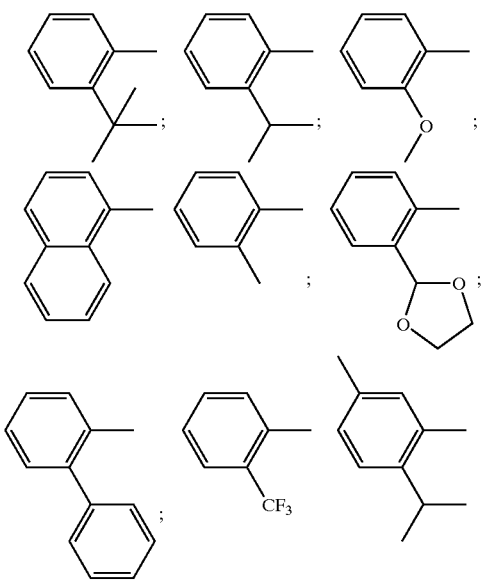

The hydrocyanation process described herein may be carried out in the presence of a catalyst precursor composition comprising a Group VIII metal and at least one multidentate phosphonite ligand having a structure III as described above and optionally a Lewis acid.

Generally, a Group VIII metal or a compound thereof is combined with at least one of the ligand structure III to provide the catalyst. Among the Group VIII metal compounds, nickel, cobalt, and palladium compounds are preferred for hydrocyanation catalysts. A nickel compound is more preferred, and a zero-valent nickel compound having a ligand that can be chemically displaced by the ligand structure of the present invention is the most preferred source of Group VIII metal or Group VIII metal compound.

Zero-valent nickel compounds that can be used for preparing the catalyst of the present invention are disclosed in the art. The preferred zero-valent nickel compounds are $Ni(COD)_2$ (COD is 1,5-cyclooctadiene), $Ni(P(O-o-C_6H_4CH_3)_3)_3$ and $Ni\{P(O-o-C_6H_4CH_3)_3\}_2(C_2H_4)$, all of which are known in the art.

The catalyst of the present invention is prepared by combining the zero-valent nickel compound with at least one molar equivalent of the ligand of structure III of the present invention in a ratio of nickel:bidentate ligand of 1:1. The ligand may be combined with nickel in a solvent, or preferably in the substrate medium. Suitable solvents include, but are not limited to, hydrocarbons such as benzene, xylene, or combinations thereof; ethers such as tetrahydrofuran (THF); nitriles such as acetonitrile, benzonitrile, adiponitrile, or combinations of two or more thereof. The unsaturated olefin used in the hydrocyanation process may itself serve as the solvent. The catalyst preparation may be done at room temperature, or at a temperature that is appropriate for the solvent being used, or the hydrocyanation process conditions.

Alternatively, divalent nickel compounds can be combined with a reducing agent, to serve as a source of zero-valent nickel in the reaction. Suitable divalent nickel compounds include compounds of the formula $NiZ^2_2$ where $Z^2$ is halide, carboxylate, or acetylacetonate. Suitable reducing agents include metal borohydrides, metal aluminum hydrides, metal alkyls, Li, Na, K, Zn or $H_2$.

The divalent nickel compound is combined with the ligand structure III of the present invention in a suitable solvent, preferably the unsaturated olefin, in a ratio of 1:1, or preferably at least 2:1. The combination is then combined with a suitable reducing agent at room temperature, or at a temperature that is appropriate for the solvent being used, or the hydrocyanation process conditions being used. The resulting catalyst composition may be isolated, if desired.

Hydrocyanation using Phosphorus-Containing Ligands of the Present Invention:

The catalyst compositions of the present invention may be used with or without a Lewis acid in the hydrocyanation of organic compounds. The hydrocyanation process comprises contacting, in the presence of the catalyst, an olefinic unsaturated organic compound with a hydrogen cyanide-containing fluid under conditions sufficient to produce a nitrile, wherein the catalyst comprises a Group VIII metal, at least one of the ligands described above, and optionally a Lewis acid as a promoter. As used herein, the term "fluid" means gas, a liquid, or a combination of these. Any fluid containing about 1 to 100% HCN can be used.

A particularly significant use of the ligands of the present invention is in the hydrocyanation of olefins. In such a process, an olefinic compound such as a diolefinic compound can be converted to a nitrile or a dinitrile, or a combination thereof. The hydrocyanation process can be carried out, for example, by charging a suitable vessel with an olefin, catalyst composition, and solvent, if used, to form a reaction mixture. Hydrogen cyanide can be combined initially with other components to form the mixture. However, it is preferred that HCN be added slowly to the mixture after other components have been combined. Hydrogen cyanide can be delivered as a liquid or as a vapor to the vessel. As an alternative, a cyanohydrin can be used as the source of HCN. See, for example, U.S. Pat. No. 3,655,723, incorporated herein by reference.

Another suitable technique is to charge the vessel with the catalyst and the solvent (if any) to be used, and feed both the unsaturated compound and the HCN slowly to the reaction mixture.

The molar ratio of ethylenically unsaturated olefin compound to catalyst can be varied from about 10:1 to about 10000:1. The molar ratio of HCN to catalyst generally is varied from about 10:1 to 100,000:1, preferably 100:1 to 5,000:1, for a batch operation. In a continuous operation, such as when using a fixed bed catalyst type of operation, a higher proportion of catalyst can be used such as a molar ratio of about 5:1 to about 100,000:1, and preferably about 100:1 to about 5,000:1, HCN to catalyst.

Preferably, the reaction mixture is agitated, for example, by stirring or shaking. The reaction product can be recovered by conventional techniques such as distillation. The process can be run either batchwise or continuously.

The hydrocyanation can be carried out with or without a solvent. The solvent, if used, can be liquid at the reaction temperature and pressure and inert towards the olefin and the catalyst. Suitable solvents include, but are not limited to, hydrocarbons such as benzene, xylene, or combinations thereof; ethers such as tetrahydrofuran (THF); nitrites such as acetonitrile, benzonitrile, adiponitrile, or combinations of two or more thereof. The unsaturated olefin to be hydrocyanated can itself serve as the solvent. Hydrocyanation can also be carried out in the gas phase.

The exact temperature is dependent to a certain extent on the particular catalyst being used, the particular olefin being used and the desired reaction rate. Normally, temperatures of from about −25° C. to about 200° C. can be used with the range of 0° C. to 150° C. being preferred.

Atmospheric pressure is suitable for carrying out the reaction, and hence pressures of from about 0.05 to 10 atmospheres (50.6 to 1013 kPa) are preferred. Higher pressures, up to 10,000 kPa or more, can be used, if desired, but any benefit that may be obtained thereby would probably not justify the increased cost of such operations.

The time required can be in the range of from a few seconds to many hours (such as 2 seconds to 24 hours), depending on the particular conditions and method of operation.

The ethylenically unsaturated olefin compound is acyclic and aliphatic, or a combination of two or more ethylenically unsaturated olefin compounds that each are acyclic and aliphatic. A non-limiting example of these compounds is shown in Formula IV, and the corresponding nitrile compound produced by the hydrocynation process is shown by Formula V, respectively.

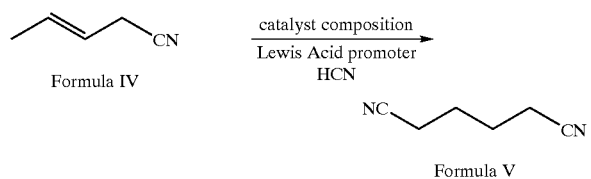

Formula IV

Formula V

The ethylenically unsaturated olefin has 2 to about 30 carbon atoms per molecule and has the formula selected from the group consisting of $R_3CH=CH—CH=CR_4$, $CH=CH—(CH_2)_q—R_5$, $CH_3—(CH_2)_n—CH=CH—(CH_2)_q—R_6$, and combinations of two or more thereof, wherein $R_3$ and $R_4$ are each independently H, C1 to C3 alkyl, or combinations thereof; $R_5$ is H, CN, $CO_2R_8$, perfluoroalkyl having 1 to about 20 carbon atoms; n is an integer of 0 to 12; q is an integer of 0 to 12 when $R_6$ is H or perfluoroalkyl, and q is an integer of 1 to 12 when $R_6$ is $CO_2R_7$, CN; and $R_7$ is C1 to C12 alkyl or cycloalkyl, C6 to C20 aryl, or combinations thereof.

Examples of suitable olefins include ethylenically unsaturated compounds such as ethylene, propylene, 1-butene, 2-pentene, 2-hexene, and combinations of two or more thereof; non-conjugated diethenically unsaturated compounds such as allene, substituted ethenically unsaturated compounds such as 3-pentenenitrile, 4-pentenenitrile, methyl pent-3-enoate, and combinations of two or more thereof; and ethenically unsaturated compounds having perfluoroalkyl substituents such as, for example, $C_bF_{2b+1}$, where b is an integer of up to 20. Preferred olefins are linear alkenes, linear alkenenitriles, linear alkenoates, perfluoroalkyl ethylenes, and combinations of two or more thereof. Most preferred olefins include 3- and 4-pentenenitrile, alkyl 3-, and 4-pentenoates, and $C_bF_{2b+1}CH=CH_2$ (where b is 1 to 12), and combinations of two or more thereof. 3-Pentenenitrile and 4-pentenenitrile are the most preferred.

The preferred products are terminal alkane nitriles, linear dicyanoalkylenes, linear aliphatic cyanoesters, 3-(perfluoroalkyl)propionitrile, and combinations of two or more thereof. Most preferred products are adiponitrile, alkyl 5-cyanovalerate, $C_bF_{2b+1}CH_2CH_2CN$, where b is 1 to 12, and combinations of two or more thereof.

The process of this invention can be carried out in the presence of one or more Lewis acid promoters to affect both the activity and the selectivity of the catalyst system. The promoter may comprise an inorganic or organometallic compound in which the cation is selected from the group consisting of scandium, titanium, vanadium, chromium, manganese, iron, cobalt, copper, zinc, boron, aluminum, yttrium, zirconium, niobium, molybdenum, cadmium, rhenium and tin. Examples include, but are not limited to, $ZnBr_2$, $ZnI_2$, $ZnCl_2$, $ZnSO_4$, $CuCl_2$, $CuCl$, $Cu(O_3SCF_3)_2$, $CoCl_2$, $CoI_2$, $FeI_2$, $FeCl_3$, $FeCl_2$, $FeCl_2(THF)_2$, $TiCl_2$, $TiCl_4(THF)_2$, $MnCl_2$, $ScCl_3$, $AlCl_3$, $(C_8H_{17})AlCl_2$, $(C_8H_{17})_2AlCl$, (iso-$C_4H_9)_2AlCl$, $Ph_2AlCl$, $PhAlCl_2$, $ReCl_5$, $ZrCl_4$, $NbCl_5$, $VCl_3$, $CrCl_2$, $MoCl_5$, $YCl_3$, $CdCl_2$, $LaCl_3$, $Er(O_3SCF_3)_3$, $Yb(O_2CCF_3)_3$, $SmCl_3$, $B(C_6H_5)_3$, $TaCl_5$. Suitable promoters known in the art. These include metal salts, such as $ZnCl_2$, $CoI_2$, and $SnCl_2$, and organometallic compounds (such as $R_8AlCl_2$, $R_8SnO_3SCF_3$, and $R_8B$, where $R_8$ is an alkyl or aryl group). U.S. Pat. No. 4,874,884 (incorporated herein by reference) describes how synergistic combinations of promoters can be chosen to increase the catalytic activity of the catalyst system. Preferred promoters include $CdCl_2$, $FeCl_2$, $ZnCl_2$, $B(C_6H_5)_3$, and $(C_6H_5)_3Sn(CF_3SO_3)$, $CH_3C_6H_5SO_3$, or $(C_6H_5)_3BCN$. The mole ratio of promoter to Group VIII metal present in the reaction can be within the range of about 1:16 to about 50:1.

Hydrocyanation can also be carried out with a conjugated ethylenically unsaturated olefin having from 4–15 carbon atoms, preferably 4 to 10 carbon atoms. With conjugated olefins, a Lewis Acid promoter is optional. Examples of conjugated olefins containing from about 4 to about 15 carbon atoms are 1,3-butadiene, cis and trans-2,4-hexadienes, cis and trans-1,3-pentadienes, and combinations of two or more thereof. Butadiene is especially preferred.

The following Formulae VI and VII illustrate some suitable starting conjugated olefins. The products of the hydrocyanation process, as described herein, of 1,3-butadiene are represented in Formulas VIII, IX, and X:

  VI

  VII (1,3-butadiene)

wherein each one of $R_9$ and $R_{10}$, independently, is H or a $C_1$ to $C_3$ alkyl;

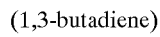  VIII

3PN

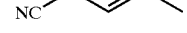  IX

4PN

  X

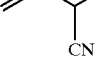

2M3BN in which 3PN denotes 3-pentenenitrile, 4PN is 4-pentenenitrile, and 2M3BN is 2-methyl-3-butenenitrile.

The reaction of a conjugated olefin and a HCN-containing fluid can be carried out in the same manner as that described above in relation to monoethenically unsaturated compounds.

The catalyst compositions of the present invention may also be used in the isomerization of allylic nitrites. The catalyst composition is combined with the allylic nitrile in a vessel and the isomerization process is carried at from 0 degrees C. to 150 degrees C., and preferably from 80 degrees C. to 120 degrees C. A solvent may be used. Examples of a suitable solvent include but are not limited to, hydrocarbons such as benzene, xylene, or combinations thereof; ethers such as tetrahydrofuran (THF); nitriles such as acetonitrile, benzonitrile, adiponitrile, or combinations of two or more thereof.

EXAMPLES

The following non-limiting, representative examples illustrate the process and catalyst compositions of this invention. All parts, proportions, and percentages are by weight, unless otherwise indicated. In each example, the following procedure was used unless otherwise noted.

Examples 1–27

Catalyst solutions were prepared by mixing one of the bidentate ligands of the invention and Ni(COD)$_2$ in a molar ratio of 1.1:1 and dissolving this in toluene. To the catalyst solution was added a solution of the promoter in the trans-3PN. The promoter: nickel molar ratio is 1.1:1. The molar ratio of trans-3PN to Ni was 200 equivalents. The reaction vessel was heated to the temperature as described in the following Tables and hydrogen cyanide was delivered by slow evaporation of the hydrogen cyanide from a reservoir connected to the reaction vessel by a feed tube in an otherwise closed reaction system. The reaction was analyzed after 15 hours. The reaction mixture was analyzed using standard Gas Chromatograph methodology. Tables I-through III list the conversion of pentenenitriles to dinitriles and the selectivity to adiponitrile, defined as the ratio of adiponitrile over all dinitriles, in this hydrocyanation reaction.

TABLE I

Promoter: ZnCl$_2$

| ligand | Conversion to Dinitrile | Selectivity to ADN |
|---|---|---|
| 50° C. | | |
| Example 1 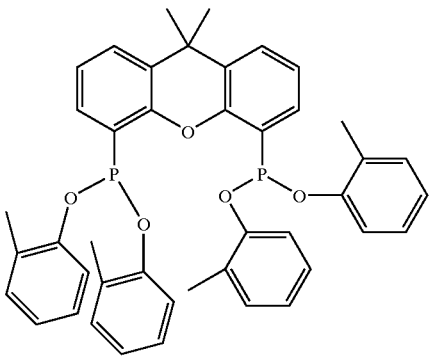 | 73.8 | 91.0 |
| Example 2 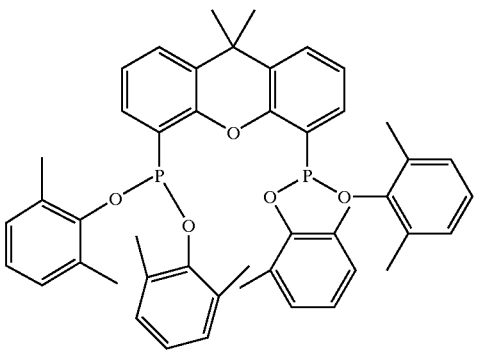 | 2.2 | 81.8 |
| Example 3 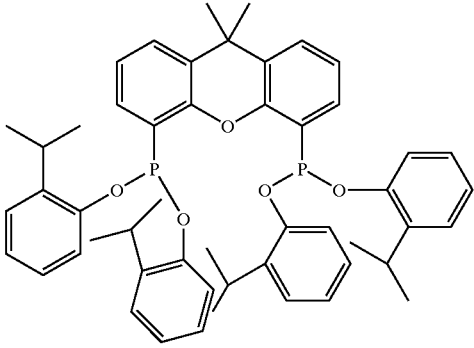 | 57.4 | 90.6 |

TABLE I-continued

Promoter: ZnCl$_2$

| ligand | Conversion to Dinitrile | Selectivity to ADN |
|---|---|---|
| Example 4 | 32.7 | 87.6 |
| Example 5 | 87.5 | 88.7 |
| Example 6 | 28.2 | 85.1 |

80° C.

| | | |
|---|---|---|
| Example 7 | 13.5 | 82.9 |

TABLE I-continued

Promoter: ZnCl$_2$

| ligand | Conversion to Dinitrile | Selectivity to ADN |
|---|---|---|
| Example 8 | 58.8 | 73.0 |
| Example 9 | 66.0 | 77.2 |
| Example 10 | 83.2 | 73.7 |

TABLE II

Promoter: ZnCl₂

| 50° C. | Ligand | Conversion to Dinitrile | Selectivity for ADN |
|---|---|---|---|
| Example 11 | [ferrocene-based diphosphite ligand with 2-tert-butylphenoxy groups] | 40.5 | 90.0 |
| Example 12 | [ferrocene-based diphosphite ligand with 2-isopropylphenoxy groups] | 83.0 | 77.2 |
| Example 13 | [ferrocene-based diphosphite ligand with 2-phenylphenoxy groups] | 74.4 | 86.2 |

TABLE III

| 80° C. | Ligand | Promoter | Conversion to Dinitrile [%] | Selectivity for ADN [%] |
|---|---|---|---|---|
| Example 14 | (OEt ligand structure) | ZnCl$_2$ | 9.0 | 73.8 |
| Example 15 | | AlCl$_3$ | 21.9 | 79.6 |
| Example 16 | | Sesqui-AlCl | 23.5 | 80.7 |
| Example 17 | | CoCl$_2$ | 11.7 | 67.4 |
| Example 18 | (OMe ligand structure) | ZnCl$_2$ | 9.8 | 80.8 |
| Example 19 | | AlCl$_3$ | 24.2 | 81.7 |
| Example 20 | | Sesqui-AlCl | 34.7 | 86.0 |
| Example 21 | | CoCl$_2$ | 12.7 | 75.9 |

Examples 22–25:

Butadiene Hydrocyanation 1,3-Butadiene Solution (BD): 1.56 g of BD were dissolved in 2 g of toluene. The resulting solution was stored in a sealed vessel at −35° C. until used.

HCN Solution: 0.93 g of liquid HCN was weighed into 1.9 g of toluene. The resulting solution was stored in a sealed vessel at −35° C. until used.

Catalyst Solution: For a typical multidentate phosphonite ligand 13 mmol of the bidentate ligand and 10 mmol of Ni(COD)$_2$ were combined in toluene to generate 3 g of catalyst solution.

In the examples as shown in Table IV, the butadiene hydrocyanation processes were carried out as described below.

To a reaction vessel were added 0.1 ml of the catalyst solution. To this was added 0.18 g of the butadiene solution followed by 0.14 g of the HCN solution. The vessel was sealed and placed in a reactor set at 100° C. Samples were removed after three hours.

Table IV lists the productive conversion of butadiene to 2M3BN, c,t-3PN, 4PN (total PN) and the ratio of 3PN/2M3BN, which was analyzed by GC method.

TABLE IV

| | % Total PN | 3PN/2M3 |
|---|---|---|
| Example 22 (structure) | 79.4 | 0.38 |
| Example 23 (structure) | 83.7 | 0.73 |
| Example 24 (structure) | 82.0 | 0.76 |

TABLE IV-continued

| | % Total PN | 3PN/2M3 |
|---|---|---|
| Example 25 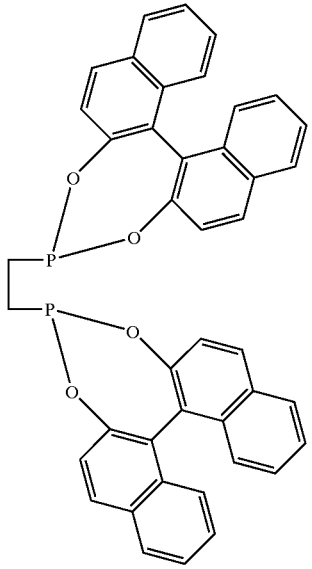 | 31.2 | 0.42 |

Examples 26–27:

Isomerization of 2-methyl-3-butenenitrile to 3-pentenenitrile

For a typical multidentate phosphonite ligand of the invention 0.008 g of Ni(COD)$_2$ was mixed with 0.032 mmol of the ligand and dissolved in 0.8 g of toluene. To this was added 0.56 g of 2M3BN. The reactor was closed and heated to 100° C. The reactions were analyzed after 4 hours and 8 hours reaction time. The reaction mixture was analyzed using standard GC methods. The ratio of 2M3BN to 3PN is listed in Table V.

TABLE V

| | | Ratio of 3PN/2M3BN | |
|---|---|---|---|
| Entry | Ligand | 4 hrs | 8 hrs |
| 1 | 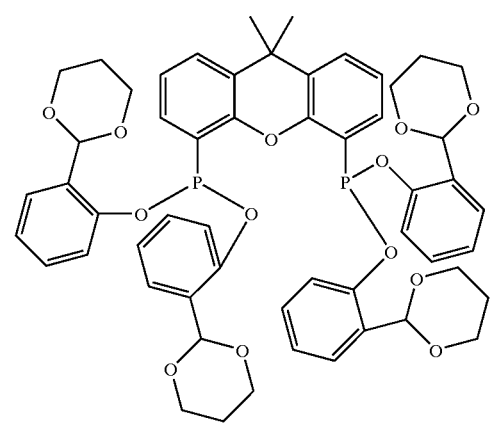 | 24.2 | 25.6 |

TABLE V-continued

| | | Ratio of 3PN/2M3BN | |
|---|---|---|---|
| Entry | Ligand | 4 hrs | 8 hrs |
| 2 | 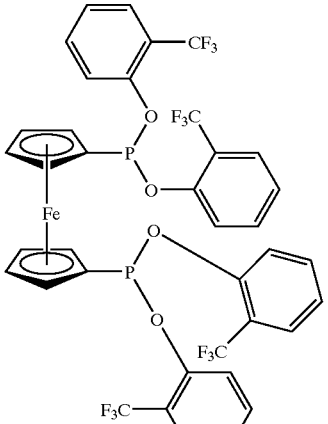 | 20.1 | 24.6 |
| 3 | 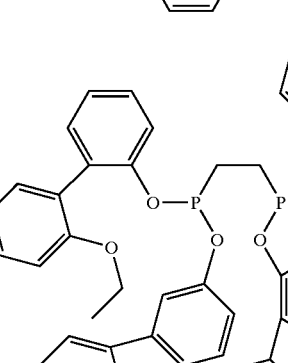 | 1.4 | 5.2 |

What is claimed is:

1. A hydrocyanation process, said process, said process comprising: contacting an acyclic and aliphatic ethylenically unsaturated olefin compound with HCN in the presence of a catalyst composition, wherein said catalyst composition comprises a Group VIII metal and a phosphonite ligand wherein the ligand has a structure:

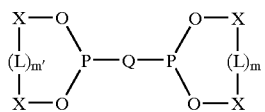

III wherein the X groups independently are selected from the group consisting of unbridged substituted and unsubstituted organic aromatic groups, and when X is substituted, the substituent on X is independently selected from the group consisting of C1 to C12 alkyl, perfluoroalkyl, cycloalkyl, alkoxy, acetal, ketal, alkylaryl, aryl, 1,3-dioxolane, cyano, and hydrogen and wherein the Q groups independently are selected from the group consisting of substituted and unsubstituted divalent aromatic and non aromatic hydrocarbon radicals, and when Q is substituted, the substituent on the Q groups is independently selected from the group consisting of C1 to C12 alkyl, cycloalkyl, alkoxy, alkylaryl, aryl, pyran, and cyano, and L is a linking group selected from the group consisting of —CR1R2-, —O—, —S—, —CO— (wherein each of R1-R2 are independent of one another, are a hydrogen atom, a C1–12 alkyl group, or an aryl group), and each of m and m' which are independent of each other, are 0 or 1.

2. A hydrocyanation process according to claim 1 wherein X is selected from the group consisting of substituted or unsubstituted phenyl, substituted or unsubstituted naphthyl, and combinations thereof.

3. A hydrocyanation process according to claim 1 wherein the X is selected from the group consisting of:

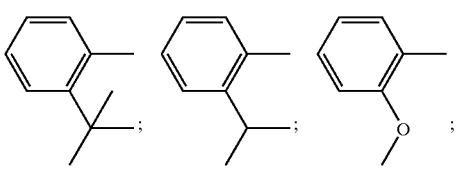

-continued

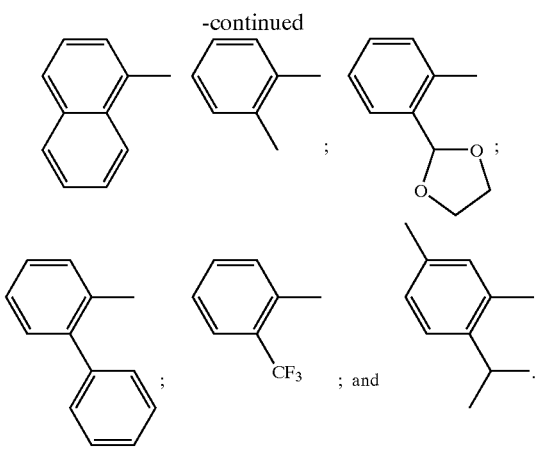

4. A hdrocyanation process according to claim 1 wherein said acyclic and aliphatic ethylenically unsaturated olefin compound is a conjugated $C_4$ to $C_{20}$ diene.

5. The process of claim 1 wherein the acyclic and aliphatic ethylenically unsaturated olefin compound is 1,3-butadiene.

6. The process of claim 1 wherein reactants are in the liquid phase.

7. The process of claim 1 wherein the Group VIII metal is selected from the group consisting of nickel, cobalt, and palladium.

8. The process of claim 1 wherein said Group VIII metal is zero-valent nickel.

9. The process of claim 1 wherein the acyclic and aliphatic ethylenically unsaturated olefin compound is 3- or 4-pentenenitrile or mixture thereof.

* * * * *